(12) United States Patent
Hawley et al.

(10) Patent No.: US 7,435,832 B2
(45) Date of Patent: Oct. 14, 2008

(54) CRYSTALS INCLUDING A MALIC ACID SALT OF A 3-PYRROLE SUBSTITUTED 2-INDOLINONE, AND COMPOSITIONS THEREOF

(75) Inventors: Michael Hawley, Saline, MI (US); Thomas J. Fleck, Scotts, MI (US); Stephen P. Prescott, Schoolcraft, MI (US); Mark T. Maloney, East Lyme, CT (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 11/740,644

(22) Filed: Apr. 26, 2007

(65) Prior Publication Data

US 2007/0191458 A1  Aug. 16, 2007

Related U.S. Application Data

(63) Continuation of application No. 10/218,985, filed on Aug. 13, 2002, now abandoned.

(60) Provisional application No. 60/312,353, filed on Aug. 15, 2001.

(51) Int. Cl.
    *C07D 209/02* (2006.01)
(52) U.S. Cl. .................................. 548/465
(58) Field of Classification Search .......... 548/465
    See application file for complete search history.

(56) References Cited

U.S. PATENT DOCUMENTS

| | | | |
|---|---|---|---|
| 5,504,216 | A | 4/1996 | Holohan et al. |
| 5,597,663 | A | 1/1997 | Pendalwar et al. |
| 5,721,359 | A | 2/1998 | Dunn et al. |
| 5,777,185 | A | 7/1998 | Belter |
| 5,910,588 | A | 6/1999 | Wangnick et al. |
| 6,066,647 | A | 5/2000 | Douglas et al. |
| 6,225,474 | B1 | 5/2001 | Matsumoto et al. |
| 6,239,141 | B1 | 5/2001 | Allen et al. |
| 6,251,355 | B1 | 6/2001 | Murata et al. |
| 6,288,057 | B1 | 9/2001 | Harkness |
| 6,316,672 | B1 | 11/2001 | Stowell et al. |
| 6,329,364 | B1 | 12/2001 | Groleau |
| 6,441,014 | B2 | 8/2002 | Talley et al. |
| 6,573,293 | B2 | 6/2003 | Tang et al. |
| 2001/0003752 | A1 | 6/2001 | Talley et al. |
| 2002/0038021 | A1 | 3/2002 | Barton et al. |
| 2002/0045746 | A1 | 4/2002 | Barton et al. |
| 2002/0156292 | A1 | 10/2002 | Tang et al. |

FOREIGN PATENT DOCUMENTS

| WO | WO92/06973 | 4/1992 |
|---|---|---|
| WO | WO93/25547 | 12/1993 |
| WO | WO01/37820 | 5/2001 |
| WO | WO01/60814 | 8/2001 |

OTHER PUBLICATIONS

Fingl et al., "The Pharmacological Basis of Therapeutics, General Principles," Goodman et al., eds., New York, NY 1975; 5th Ed., Chap. 1, pp. 1-46.

Garrido, J., "Form and Structure of Crystals," *Alhambra Editorial*, Mexico (1973), pp. 204-225, and English translation (27 pgs.).

Gennaro, A., "Remington: The Scie3nce and Practice of Pharmacy," 19th Edition, Chapter 83: *Preformulation*, Mack Publishing Company, Easton, PA (1995), pp. 1447-1462.

Gennaro, J., "Remington: The Science and Practice of Pharmacy," 20th Edition, Chapter 13, pp. 159-182, *Lippincon Williams & Wilkins*, Philadelphia, PA, (2000).

Giron, D., "Investigations of Polymorphism and Pseudo-Polymorphism in Pharmaceuticals by Combined Thermoanalytical Techniques," *Journal of Therm. Anal. Calorim*, 64:37-60 (2001).

Giron, D., "Thermal Analysis and Calorimetric Methods in the Characterization of Polymorphs and Solvates," *Thermochim. Acta*, 248:1-59(1995).

Hogberg et al., *Journal of Organic Chemistry*, 1987; 52:2033-2036.

King, R., "Remington: The Science and Practice of Pharmacy," Chapter 7: *Pharmaceutical Preparations and Their Elaboration*, pp. 2226, and English translation (2 pgs).

Moscoso, A., "Intellectual Property and Technological Innovation in Ecuador," *Abya-Yala*, Quito, Ecuador (2000), pp. 35-39, and English translation (3 pgs).

*Remington's Pharmacological Sciences*, 18th Ed., Mack Publishing Co., Easton, PA (1990), cover page, copyright page, and Table of Contents (6 pgs. total).

Verma, A., "Polymorphism and Polytypism in Crystals," Wiley, NY (1966), Title page, copyright page and table of contents only.

Cheronis, N., "Semicro Experimental Organic Chemistry," 1958, Chapter 5.

"Material Safety Data Sheet for tetrahexylammonium benzoate" [online]. Acros Organics N.V., Fair Lawn, NJ, Revision #2 Date: Mar. 18, 2003 [retrieved on 2204-09-03]. Retrieved from the Internet: URL:https://fscimage.fishersci.com/msds/59424.htm, 5 pgs.

*Primary Examiner*—Rei-tsang Shiao
(74) *Attorney, Agent, or Firm*—Bryan C. Zielinski; Stephen D. Prodnuk (57) ABSTRACT

The present invention provides crystals, and compositions thereof, wherein the crystals include a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide. Methods of preparing such crystals are also disclosed.

6 Claims, 4 Drawing Sheets

CRYSTALS INCLUDING A MALIC ACID SALT OF A 3-PYRROLE SUBSTITUTED 2-INDOLINONE, AND COMPOSITIONS THEREOF

This application claims the benefit of the U.S. Provisional Application Ser. No. 60/312,353, filed Aug. 15, 2001, which is incorporated herein by reference in its entirety.

FIELD OF THE INVENTION

The present invention relates to crystals, and compositions thereof, wherein the crystals include a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide. The present invention also relates to methods of preparing such crystals.

BACKGROUND

PKs are enzymes that catalyze the phosphorylation of hydroxy groups on tyrosine, serine, and threonine residues of proteins. The consequences of this seemingly simple activity are staggering: cell growth, differentiation, and proliferation, i.e., virtually all aspects of cell life in one way or another, depend on PK activity. Furthermore, abnormal PK activity has been related to a host of disorders, ranging from relatively non-life threatening diseases such as psoriasis to extremely virulent diseases such as glioblastoma (brain cancer). The PKs can be conveniently broken down into two classes, the protein tyrosine kinases (PTKs) and the serine-threonine kinases (STKs).

One of the prime aspects of PTK activity is their involvement with growth factor receptors. Growth factor receptors are cell-surface proteins. When bound by a growth factor ligand, growth factor receptors are converted to an active form, which interacts with proteins on the inner surface of a cell membrane. This leads to phosphorylation on tyrosine residues of the receptor and other proteins and to the formation inside the cell of complexes with a variety of cytoplasmic signaling molecules that, in turn, effect numerous cellular responses such as cell division (proliferation), cell differentiation, cell growth, expression of metabolic effects to the extracellular microenvironment, etc.

Small molecules that act as PK inhibitors have been identified and include, for example, 3-pyrrole substituted 2-indolinone compounds as disclosed in PCT International Publication No. WO 01/60814 (Tang et al.). 3-Pyrrole substituted 2-indolinone compounds include, for example, N-[2-(diethylamino)ethyl]-5-[(5-fluoro-1,2-dihydro-2-oxo-3H-indol-3-ylidene)methyl]-2,4-dimethyl-1H-pyrrole-3-carboxamide as disclosed in PCT International Publication No. WO 01/60814 (Tang et al.). However, the disclosure is silent as to the preparation of and the nature of specific crystal forms of salts of N-[2-(diethylamino)ethyl]-5-[(5-fluoro-1,2-dihydro-2-oxo-3H-indol-3-ylidene)methyl]-2,4-dimethyl-1H-pyrrole-3-carboxamide. There exists a need for crystalline forms of such materials that have superior chemical and/or physical properties that are useful in drug delivery applications.

SUMMARY OF THE INVENTION

In one aspect, the present invention provides a crystal including a malic acid salt of a compound having the structure:

The compound with the above structure is also known as N-[2-(diethylamino)ethyl]-5-[(5-fluoro-1,2-dihydro-2-oxo-3H-indol-3-ylidene)methyl]-2,4-dimethyl-1H-pyrrole-3-carboxamide. The malic acid salt may be a salt of D-malic acid; D,L-malic acid; L-malic acid; or combinations thereof. Preferably, the malic acid salt is a salt of L-malic acid. Preferably, the crystal is anhydrous. Preferably, the crystal has characteristic diffraction peaks at about 13.2 and 24.2 degrees two-theta, and more preferably at about 13.2, 19.4, 24.2, and 25.5 degrees two-theta, and most preferably as listed in Table 1 for Crystal Form I, in a powder X-ray diffraction pattern. Preferably, the crystal includes at most about 2% by weight water, more preferably at most about 0.5% by weight water, and most preferably at most about 0.2% by weight water. Preferably, the crystal has a melting point of at least about 190° C., and more preferably at least about 195° C. Compositions including the crystals described herein are also provided. Preferably, the compositions include a therapeutically effective amount of the crystals. Optionally, the compositions include an excipient, preferably a pharmaceutically acceptable excipient.

In another aspect, the present invention provides a crystal including a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide, wherein the crystal has characteristic diffraction peaks at about 3.0 and 27.7 degrees two-theta, more preferably at about 3.0, 12.1, 14.5, and 27.7 degrees two-theta, and most preferably as listed in Table 1 for Crystal Form II, in a powder X-ray diffraction pattern. Typically, the crystal absorbs at least about 5% by weight water upon exposure to 80% relative humidity and has a melting point of at most about 185° C. Compositions including the crystals described herein are also provided. Preferably, the compositions include a therapeutically effective amount of the crystals. Optionally, the compositions include an excipient, preferably a pharmaceutically acceptable excipient.

In another aspect, the present invention provides methods of preparing an anhydrous crystal including a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide (e.g., Crystal Form I). In one embodiment, the method includes: combining malic acid; N-[2-(diethylamino)ethyl]-5-[(5-fluoro-1,2-dihydro-2-oxo-3H-indol-3-ylidene)methyl]-2,4-dimethyl-1H-pyrrole-3-carboxamide; and a solvent; and inducing the salt to crystallize under crystallization conditions (e.g., Crystal Form I crystallization conditions) including one or more factors including: a difference between the initial and final temperatures of the crystallization solution of at most about 100° C.; a rate of cooling of at most about 50° C. per hour; no seeding; a supersaturation ratio of at most about 10; no precipitant; and/or combinations thereof. Preferably, the malic acid is L-malic acid. Preferably, the solvent includes one or more solvents including, for example, acetonitrile, methanol, ethanol, isopropanol, toluene, n-butanol, tetrahydrofuran, N,N-dimethylformamide, acetone, water, and combinations thereof.

In another embodiment, the method of preparing an anhydrous crystal including a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide (e.g., Crystal Form I) includes: contacting a crystal including a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide with a solvent in which the contacting crystal has substantial solubility, wherein the contacting crystal (e.g., Crystal Form II) has characteristic diffraction peaks at about 3.0 and 27.7 degrees two-theta in a powder X-ray diffraction pattern. Preferably, the solvent includes one or more solvents including, for example, acetonitrile, ethanol, methanol, and combinations thereof. Preferably, contacting the crystal with the solvent forms a slurry, and the slurry is preferably stirred and/or heated. Optionally, the anhydrous crystal may be removed from the slurry.

In another aspect, the present invention provides a method of preparing a crystal including a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide (e.g., Crystal Form II). The method includes: combining malic acid; N-[2-(diethylamino)ethyl]-5-[(5-fluoro-1,2-dihydro-2-oxo-3H-indol-3-ylidene)methyl]-2,4-dimethyl-1H-pyrrole-3-carboxamide; and a solvent; and inducing the salt to crystallize under crystallization conditions (e.g., Crystal Form II crystallization conditions) including one or more factors including: a difference between the initial and final temperatures of the crystallization solution of at least about 25° C.; a rate of cooling of at least about 25° C. per hour; seeding; a supersaturation ratio of at least about 2; presence of a precipitant; and/or combinations thereof. Preferably, the malic acid is L-malic acid. Preferably, the solvent includes one or more solvents including, for example, methanol, water, tetrahydrofuran/water mixtures, and combinations thereof. Preferably, the crystal has characteristic diffraction peaks at about 3.0 and 27.7 degrees two-theta in a powder X-ray diffraction pattern.

The anhydrous Crystal Form I is advantageous over Crystal Form II for many applications because the properties that Crystal Form I offers preferably include, for example, greater thermodynamic stability, higher crystallinity, and lower hygroscopicity than the respective properties of Crystal Form II.

Numerous factors effect crystallization conditions, and they are well known to one of skill in the art. Such factors include, for example: the concentration of the salt in the crystallization solution; the difference, if any, between the initial and final temperatures of the crystallization solution; the rate of cooling, if any; the solvent vaporization rate, if any; seeding; supersaturation ratio; and presence of a precipitant. With guidance from the disclosure provided herein, one of skill in the art, without undue experimentation, may select and/or adjust one or more appropriate factors to arrive at crystallization conditions to provide Crystal Form I and/or Crystal Form II.

Definitions

As used herein, "supersaturation ratio" refers to the ratio of the concentration of the material in solution to the concentration of the material in a saturated solution at the crystallization temperature.

As used herein, "seeding" refers to the technique of adding a "seed" crystal to the crystallization solution to promote the formation of crystals. Preferably, the composition of the seed crystal is the same as the composition of the crystals being formed.

As used herein, "precipitant" means a substance that tends to induce crystallization when added to a crystallization solution. Useful precipitants include, for example, non-solvents for the salt and solutions including excess counterions. As used herein, a non-solvent is a solvent in which the salt preferably has a solubility of at most about 1% by weight, more preferably at most about 0.1% by weight, and most preferably at most about 0.01% by weight.

As used herein, "anhydrous crystal" means a crystal in which water is not specifically bound. Anhydrous crystals preferably do not include substantial amounts of water. The water content can be determined by methods known in the art including, for example, Karl Fischer titrations. Preferably an anhydrous crystal includes at most about 2% by weight water, more preferably at most about 0.5% by weight water, and most preferably at most about 0.2% by weight water.

As used herein, "crystalline" means a material that has an ordered, long range molecular structure. The degree of crystallinity of a crystal form can be determined by many techniques including, for example, powder X-ray diffraction, moisture sorption, differential scanning calorimetry, solution calorimetry, and dissolution properties.

As used herein, "more crystalline" means that a material has a higher degree of crystallinity than the material to which it is being compared. Materials with higher degrees of crystallinity generally have highly ordered, long range molecular structure with fewer defects in the crystal structure than materials with lower degrees of crystallinity. The higher degree of crystallinity can be assessed relative to the other form by techniques including, for example, sharper reflections in the powder X-ray diffraction pattern, lower moisture sorption for similar sized particles at a specified relative humidity, lower heat of solution, higher heat of fusion, slower dissolution rate, and combinations thereof.

As used herein, "less crystalline" means that a material has a lower degree of crystallinity than the material to which it is being compared. Materials with lower degrees of crystallinity generally have less long range order and more defects in the crystal structure than materials with higher degrees of crystallinity. The lower degree of crystallinity can be assessed relative to the other form by techniques including, for example, broader and/or fewer reflections in the powder X-ray diffraction pattern, higher moisture sorption for similar sized particles at a specified relative humidity, higher heat of solution, lower heat of fusion, faster dissolution rate, and combinations thereof.

As referred to in the present application, "stable" in bulk drug stability tests means that at least about 97% by weight, preferably at least about 98% by weight, and more preferably at least about 99% by weight of the bulk drug remains unchanged after storage under the indicated conditions for the indicated time.

BRIEF DESCRIPTION OF THE FIGURES

FIG. 2 is an illustration of the powder X-ray diffraction (PXRD) data for Crystal Form II of the L-malic acid salt of

N-[2-(diethylamino)ethyl]-5-[(5-fluoro-1,2-dihydro-2-oxo-3H-indol-3-ylidene)methyl]-2,4-dimethyl-1H-pyrrole-3-carboxamide. The pattern is distinct from other crystal forms of the salt and the free base, and is less crystalline than Crystal Form I as evidenced by the broader reflections in the powder X-ray diffraction pattern (e.g., FIG. 1).

DETAILED DESCRIPTION OF PREFERRED EMBODIMENTS

N-[2-(diethylamino)ethyl]-5-[(5-fluoro-1,2-dihydro-2-oxo-3H-indol-3-ylidene)methyl]-2,4-dimethyl-1H-pyrrole-3-carboxamide is a 3-pyrrole substituted 2-indolinone compound having the following structure:

N-[2-(diethylamino)ethyl]-5-[(5-fluoro-1,2-dihydro-2-oxo-3H-indol-3-ylidene)methyl]-2,4-dimethyl-1H-pyrrole-3-carboxamide can be prepared as the free base by standard synthetic procedures including, for example, those disclosed in PCT International Publication No. WO 01/60814 (Tang et al.). Although the free base may be crystallized as small particles, it is desirable in large scale operations, for example, to have larger particle size crystals for ease in filtration. To this end, the preparation of salts of N-[2-(diethylamino)ethyl]-5-[(5-fluoro-1,2-dihydro-2-oxo-3H-indol-3-ylidene)methyl]-2,4-dimethyl-1H-pyrrole-3-carboxamide was undertaken for evaluation of the resulting properties related to the processing of the salt and the preparation of oral pharmaceutical compositions therefrom.

Crystalline forms of N-[2-(diethylamino)ethyl]-5-[(5-fluoro-1,2-dihydro-2-oxo-3H-indol-3-ylidene)methyl]-2,4-dimethyl-1H-pyrrole-3-carboxamide including the free base and salts thereof (e.g., cyclamic acid, maleic acid, hydrobromic acid, mandelic acid, tartaric acid, fumaric acid, ascorbic acid, phosphoric acid, hydrochloric acid, p-toluenesulfonic acid, citric acid, and malic acid salts) were screened for properties related to the processing of the salt and the preparation of oral pharmaceutical compositions therefrom, including, for example, crystallinity (e.g., crystalline or amorphous, degree of crystallinity, anhydrous or hydrated crystals), toxicity, hygroscopicity, stability, and morphology. Based on the above screening, a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide was determined to provide the best balance of desired properties. Upon further study, it was found that a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide crystallized in multiple crystal forms.

The present invention provides methods for preparing crystal forms including a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide, and the identification of those crystal forms. The preparation of anhydrous crystals including a malic acid salt is described herein. The anhydrous Crystal Form I has superior properties for many applications.

Crystal Form I

In one embodiment, a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide has been prepared as anhydrous crystals (e.g., Crystal Form I). The anhydrous Crystal Form I is thermodynamically more stable than other crystal forms (e.g., Crystal Form II). In one method, Crystal Form I can be prepared, for example, by inducing crystallization of a malic acid salt under Crystal Form I crystallization conditions from a supersaturated solution.

As used herein, "Crystal Form I crystallization conditions" refer to crystallization conditions that provide the thermodynamic crystal form (e.g., Crystal Form I). Such conditions are commonly called "slow" crystallization conditions. One of skill in the art may select one or more factors including, for example: a difference between the initial and final temperatures of the crystallization solution of preferably at most about 100° C., more preferably at most about 50° C., even more preferably at most about 25° C., and most preferably about 0° C.; a cooling rate of preferably at most about 50° C. per hour, more preferably at most about 20° C. per hour, even more preferably at most about 2° C. per hour, and most preferably about 0° C. per hour; no seeding; a supersaturation ratio of preferably at most about 10, more preferably at most about 5, and most preferably at most about 1.5; no precipitant; and/or combinations thereof to provide for Crystal Form I crystallization conditions.

Useful solvents for preparing the crystallization solution include, for example, acetonitrile, methanol, ethanol, isopropanol, toluene, n-butanol, tetrahydrofuran, N,N-dimethylformamide, acetone, water, and combinations thereof.

In another method, Crystal Form I can be prepared, for example, by providing a slurry of Crystal Form II in solvents in which Crystal Form II has substantial solubility. As used herein, "substantial solubility" means that a crystal is preferably soluble in the solvent in concentrations of at least about 0.1% by weight, more preferably at least about 1% by weight, and most preferably at least about 10% by weight, at about room temperature (e.g., about 15° C. to about 30° C.). Optionally, the crystal can be dissolved in the solvent at the indicated concentration at room temperature.

Such solvents include, for example, acetonitrile, ethanol, methanol, and combinations thereof.

Crystal Form II

In another embodiment, a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide has been prepared in another crystalline form (e.g., Crystal Form II). Crystal Form II is useful, for example, as an intermediate in the preparation of the anhydrous Crystal Form I.

Crystal Form II can be prepared, for example, by inducing a malic acid salt to crystallize under Crystal Form II crystallization conditions from a supersaturated solution.

As used herein, "Crystal Form II crystallization conditions" refer to crystallization conditions that provide a crystal form other than the thermodynamic form. Such conditions are commonly called "rapid" crystallization conditions. One of skill in the art may select one or more factors including, for example: a difference between the initial and final temperatures of the crystallization solution of preferably at least about 25° C., more preferably at least about 50° C., and most preferably at least about 100° C.; a rate of cooling of preferably at least about 25° C. per hour, more preferably at least about 100° C. per hour, and most preferably at least about 300° C. per hour; seeding; a supersaturation ratio of preferably at least about 2, more preferably at least about 5, and most preferably at least about 10; presence of a precipitant; and/or combinations thereof to provide for Crystal Form II crystallization conditions.

Useful solvents for the crystallization solution include, for example, methanol, water, tetrahydrofuran/water mixtures, and combinations thereof.

Powder X-Ray Diffraction (PXRD)

Crystalline organic compounds consist of a large number of atoms that are arranged in a periodic array in three-dimensional space. The structural periodicity normally manifests distinct physical properties, such as sharp, explicit spectral features by most spectroscopic probes (e.g., X-ray diffraction, infrared and solid state NMR). X-ray diffraction (XRD) is acknowledged to be one of the most sensitive methods to determine the crystallinity of solids. Crystals yield explicit diffraction maxima that arise at specific angles consistent with the lattice interplanar spacings, as predicted by Bragg's law. On the contrary, amorphous materials do not possess long-range order. They often retain additional volume between molecules, as in the liquid state. Amorphous solids normally unveil a featureless XRD pattern with broad, diffuse halos because of the absence of the long range order of repeating crystal lattice.

Powder X-ray diffraction has been reportedly been used to characterize different crystal forms of organic compounds (e.g., compounds useful in pharmaceutical compositions). See, for example, U.S. Pat. Nos. 5,504,216 (Holohan et al), 5,721,359 (Dunn et al.), 5,910,588 (Wangnick et al.), 6,066,647 (Douglas et al.), 6,225,474 (Matsumoto et al.), 6,239,141 (Allen et al.), 6,251,355 (Murata et al.), 6,288,057 (Harkness), 6,316,672 (Stowell et al.), 6,329,364 (Groleau), and U.S. Pat. Application Publication Nos. 2001/0003752 (Talley et al.), 2002/0038021 (Barton et al.), and 2002/0045746 (Barton et al.).

Crystalline materials are preferred in many pharmaceutical applications. Crystalline forms are generally thermodynamically more stable than amorphous forms of the same substance. This thermodynamic stability is preferably reflected in the lower solubility and improved physical stability of the crystalline form. The regular packing of the molecules in the crystalline solid preferably denies the incorporation of chemical impurities. Hence crystalline materials generally possess higher chemical purity than their amorphous counterparts. The packing in the crystalline solid generally constrains the molecules to well defined lattice positions and reduces the molecular mobility that is the prerequisite for chemical reactions. Hence, crystalline solids, with very few notable exceptions, are chemically more stable than amorphous solids of the same molecular composition. Preferably, the crystalline forms of malic acid salts N-[2-(diethylamino)ethyl]-5-[(5-fluoro-1,2-dihydro-2-oxo-3H-indol-3-ylidene)methyl]-2,4-dimethyl-1H-pyrrole-3-carboxamide disclosed in the present application possess one or more of the advantageous chemical and/or physical properties disclosed herein.

The crystalline forms of malic acid salts of N-[2-(diethylamino)ethyl]-5-[(5-fluoro-1,2-dihydro-2-oxo-3H-indol-3-ylidene)methyl]-2,4-dimethyl-1H-pyrrole-3-carboxamide disclosed in the present application preferably have distinct powder X-ray diffraction profiles. For example, the anhydrous crystals including a malic acid salt of the N-[2-(diethylamino)ethyl]-5-[(5-fluoro-1,2-dihydro-2-oxo-3H-indol-3-ylidene)methyl]-2,4-dimethyl-1H-pyrrole-3-carboxamide can preferably be distinguished from the other crystal form including a malic acid salt disclosed herein by the presence of characteristic diffraction peaks. Characteristic diffraction peaks as used herein are peaks selected from the most intense peaks of the observed diffraction pattern. Preferably, the characteristic peaks are selected from about 20 of the most intense peaks, more preferably from about 10 of the most intense peaks, and most preferably from about 5 of the most intense peaks in the diffraction pattern.

Figure 1:
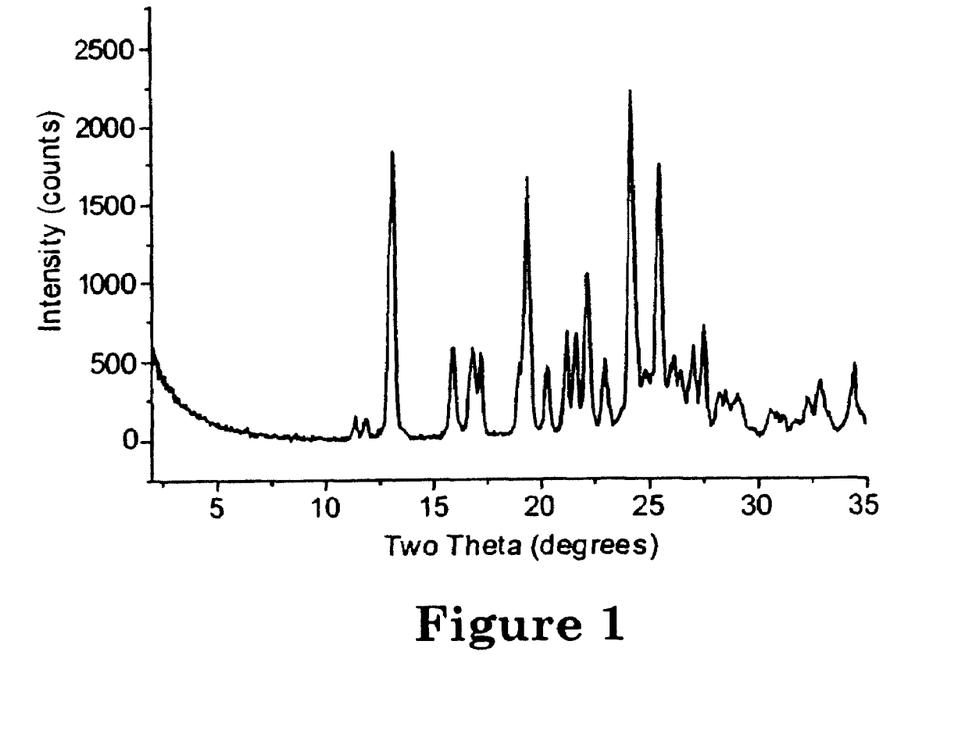
FIG. 1 is an illustration of the powder X-ray diffraction (PXRD) data for Crystal Form I of the L-malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide. The pattern is distinct from other crystal forms of the salt and the free base, and is more crystalline than Crystal Form II (e.g., FIG. 2).
Figure 2:
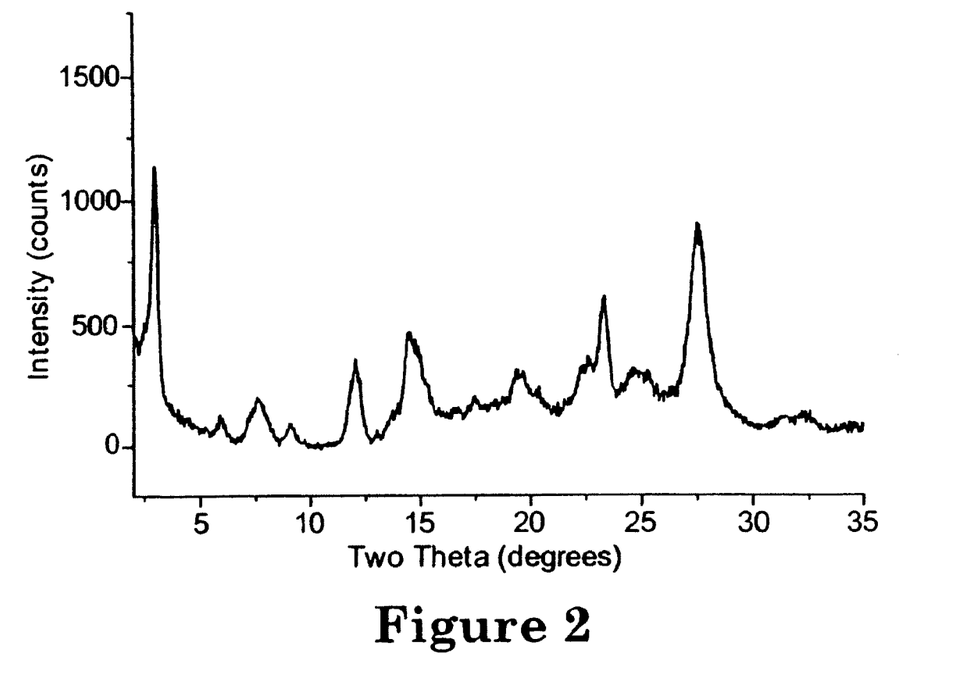

FIGS. 1 and 2 show the powder X-ray diffraction patterns for Crystal Forms I and II, respectively, of the L-malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide. Table 1 contains the listing of the most intense peaks from each PXRD pattern between 2 and 35 degrees two theta. The free base, Crystal Form I, and Crystal Form II are all easily distinguished by their unique PXRD patterns.

Preferably an anhydrous crystal including a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide (e.g., Crystal Form I) has characteristic diffraction peaks at about 13.2 and 24.2 degrees two-theta, more preferably at about 13.2, 19.4, 24.2, and 25.5 degrees two-theta, and most preferably has the characteristic diffraction peaks as listed in Table 1 for Crystal Form I.

Preferably, Crystal Form II of a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide has characteristic diffraction peaks at about 3.0 and 27.7 degrees two-theta, more preferably at about 3.0, 12.1, 14.5, and 27.7 degrees two-theta, and most preferably has the characteristic diffraction peaks as listed in Table 1 for Crystal Form II.

TABLE 1

Powder X-Ray Diffraction Peak Table for Crystal Forms I and II

| Crystal Form I | | Crystal Form II | |
|---|---|---|---|
| Two Theta (deg.) | Relative Intensity | Two Theta (deg.) | Relative Intensity |
| 11.39 | 7 | 3.02 | 100 |
| 11.90 | 7 | 5.93 | 12 |
| 13.16 | 82 | 7.61 | 18 |
| 15.92 | 27 | 9.26 | 7 |
| 16.79 | 25 | 12.08 | 32 |
| 17.18 | 24 | 14.54 | 42 |
| 19.40 | 76 | 17.54 | 19 |
| 20.30 | 20 | 19.46 | 28 |
| 21.26 | 31 | 23.36 | 54 |
| 21.68 | 28 | 24.77 | 28 |
| 22.13 | 48 | 27.71 | 80 |
| 22.91 | 21 | | |
| 24.17 | 100 | | |
| 25.46 | 79 | | |
| 26.06 | 23 | | |
| 26.96 | 26 | | |
| 27.56 | 28 | | |
| 32.27 | 13 | | |
| 32.93 | 17 | | |
| 34.43 | 23 | | |

Purity and Solid State Stability

The purity of Crystal Form I of a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide was evaluated by high pressure liquid chromatography (HPLC). The results showed greater than about 98 area % purity with less than about 2 area % impurities detected (Table 2).

A solid state stability study of Crystal Form I of the L-malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide was also conducted (Table 2). Four week data after aging at 60° C./ambient relative humidity, 60° C./75% relative humidity, and 80° C./ambient relative humidity showed no significant degradation. Powder X-ray diffraction on two-week samples also indicated no change in crystal form.

TABLE 2

Stability of Crystal Form I based on HPLC Analysis

| Condition | Purity (Area %) | Total Impurities (Area %) |
|---|---|---|
| Initial | 99.7 | 1.5 |
| 2 weeks at 60° C./ambient RH* | 98.2 | 1.1 |
| 2 weeks at 60° C./75% RH | 99.6 | 1.2 |
| 2 weeks at 80° C./ambient RH | 99.5 | 1.2 |
| 4 weeks at 60° C./ambient RH | 100.4 | 1.2 |
| 4 weeks at 60° C./75% RH | 100.1 | 2.2 |
| 4 weeks at 80° C./ambient RH | 98.0 | 3.1 |

*relative humidity (RH)

Moisture Sorption Data

Figure 3:
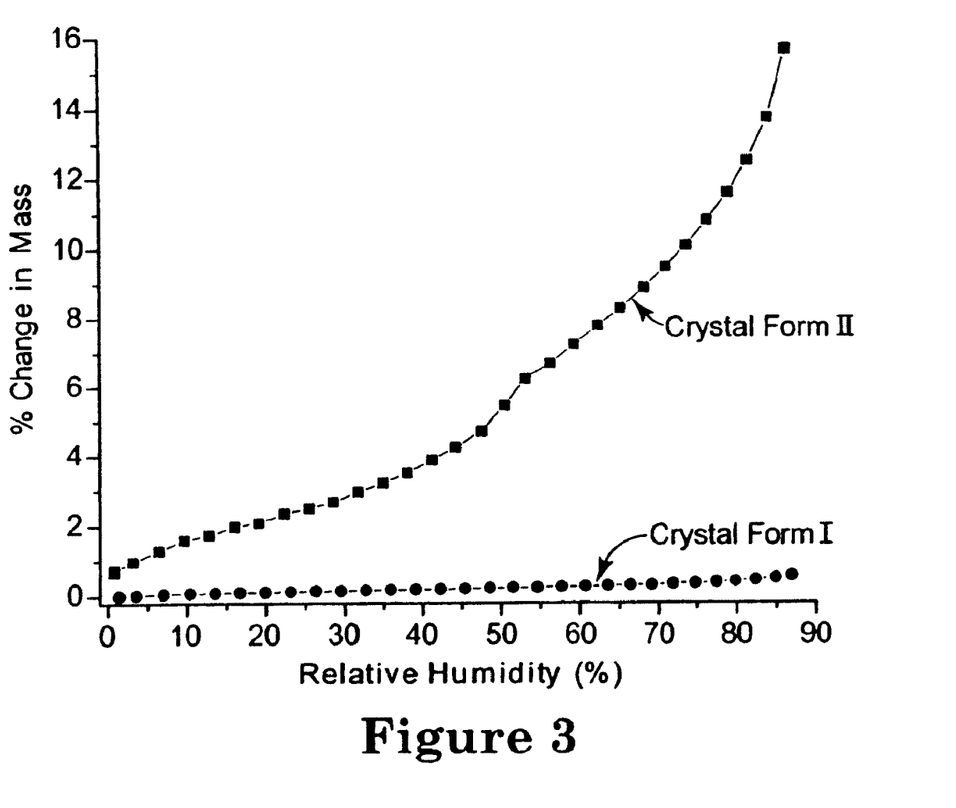
FIG. 3 is an illustration of dynamic moisture sorption gravimetry (DMSG) sorption isotherm for Moisture sorption profiles for Crystal Form I & Crystal Form II of the L-malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide. The more crystalline polymorph, Crystal Form I is of low hygroscopicity, absorbing less than 0.5% water across the 0-90% relative humidity range. The less crystalline polymorph, Crystal Form II, is very hygroscopic, absorbing over 15% water over the 0-90% relative humidity range.

The moisture sorption data at 25° C. for Crystal Forms I and II of the L-malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide are shown in FIG. 3. The more crystalline polymorph, Crystal Form I is of low hygroscopicity, absorbing less than 0.5% water across the 0-90% relative humidity range. The less crystalline polymorph, Crystal Form II, is very hygroscopic, absorbing over 15% water over the 0-90% relative humidity range.

Thermal Data

Figure 4:
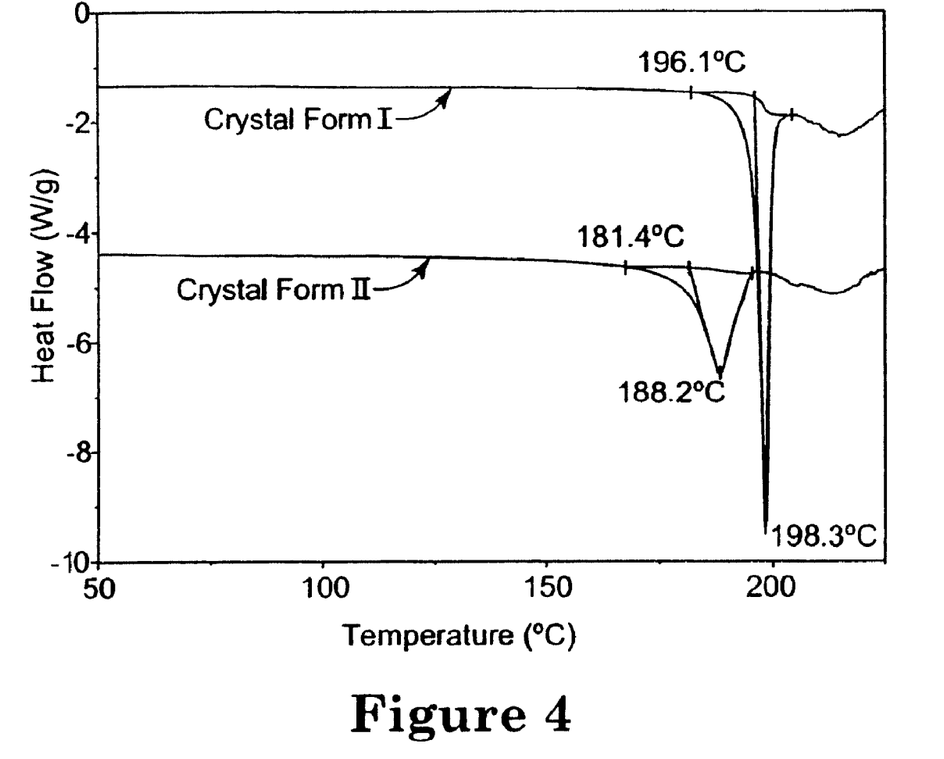
FIG. 4 is an illustration of differential scanning calorimetry (DSC) data showing DSC profiles for Crystal Form I & Crystal Form II of the L-malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide. Exothermic transitions are indicated in the up direction. Crystal Form I melts at a higher temperature (about 196° C.) with a higher melt enthalpy (about 141 J/g) than Crystal Form II, which melts at about 181° C. with a melt enthalpy of about 105 J/g. This suggests the two crystal forms are monotropic, although degradation occurs after the crystals melt. Monotropism is confirmed by the conversion of Crystal Form II to Crystal Form I in a room temperature slurry as described herein.

The differential scanning calorimetry data is shown in FIG. 4. The anhydrous Crystal Form I of the L-malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide melts at about 196° C., while Crystal Form II melts at about 181° C. The events observed after the initial melt suggest that there is probably some decomposition associated with the melting. Therefore, an accurate heat of fusion could not be readily measured.

The TGA data for Crystal Form I (not shown) showed no significant weight loss up to the melting point, indicating the lack of residual solvent and/or water retained in the crystals.

Administration and Pharmaceutical Compositions

Crystals of the present invention can be administered as such to a human patient or can be administered in pharmaceutical compositions in which the foregoing crystal is mixed with suitable carriers or excipient(s). Techniques for formulation and administration of drugs may be found in "Remington's Pharmacological Sciences," Mack Publishing Co., Easton, Pa., latest edition.

As used herein, "administer" or "administration" refers to the delivery of a crystal of the present invention or a pharmaceutical composition thereof to an organism for the purpose of prevention or treatment of a PK-related disorder.

Suitable routes of administration may include, without limitation, oral, rectal, transmucosal or intestinal administration or intramuscular, subcutaneous, intramedullary, intrathecal, direct intraventricular, intravenous, intravitreal, intraperitoneal, intranasal, or intraocular injections. The preferred routes of administration are oral and parenteral.

Alternatively, one may administer the crystal of the present invention or a pharmaceutical composition thereof in a local rather than systemic manner, for example, via injection of the crystal of the present invention or a pharmaceutical composition thereof directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers including excipients and auxiliaries that facilitate processing of crystals of the present invention into preparations that can be used pharmaceutically. Proper formulation is dependent upon the route of administration chosen.

For injection, a crystal of the present invention or a pharmaceutical composition thereof may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, a crystal of the present invention or a pharmaceutical composition thereof can be formulated by combining a crystal of the present invention with pharmaceutically acceptable carriers well known in the art. Such carriers enable crystals of the present invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active doses.

Pharmaceutical compositions that can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, crystals of the present invention may be dissolved or suspended in suitable liquids, such as fatty oils, liquid paraffin, or liquid polyethylene glycols. Stabilizers may be added in these formulations, also.

The capsules may be packaged into brown glass or plastic bottles to protect crystals of the present invention or pharmaceutical compositions thereof from light. The containers containing the active capsule formulation must be stored at controlled room temperature (e.g., about 15° C. to about 30° C.).

For administration by inhalation, a crystal of the present invention or a pharmaceutical composition thereof is conveniently delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of a crystal of the present invention or a pharmaceutical composition thereof, and a suitable powder base such as lactose or starch.

A crystal of the present invention or a pharmaceutical composition thereof may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulating materials such as suspending, stabilizing, and/or dispersing agents.

Pharmaceutical compositions for parenteral administration include aqueous solutions of a water soluble form of a crystal of the present invention or pharmaceutical composition thereof. Additionally, suspensions of crystals of the present invention or pharmaceutical compositions thereof may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Optionally, the suspension may also contain suitable stabilizers and/or agents that increase the solubility of the crystals of the present invention or a pharmaceutical composition thereof to allow for the preparation of highly concentrated solutions.

Alternatively, the active ingredient may be in powder form for constitution with a suitable vehicle, e.g., sterile, pyrogen-free water, before use.

A crystal of the present invention or a pharmaceutical composition thereof may also be formulated in rectal compositions such as suppositories or retention enemas, using, e.g., conventional suppository bases such as cocoa butter or other glycerides.

In addition to the formulations described previously, a crystal of the present invention or a pharmaceutical composition thereof may also be formulated as depot preparations. Such long acting formulations may be administered by implantation (for example, subcutaneously or intramuscularly) or by intramuscular injection. A crystal of the present invention or a pharmaceutical composition thereof may be formulated for this route of administration with suitable polymeric or hydrophobic materials (for instance, in an emulsion with a pharamcologically acceptable oil), with ion exchange resins, or as a sparingly soluble derivative.

Additionally, a crystal of the present invention or a pharmaceutical composition thereof may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release a salt or a pharmaceutical composition thereof for a few weeks up to over 100 days. Depending on the chemical nature and the biological stability of the therapeutic reagent, additional strategies for protein stabilization may be employed.

The pharmaceutical compositions herein also may include suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in an amount sufficient to achieve the intended purpose, e.g., the modulation of PK activity or the treatment or prevention of a PK-related disorder.

More specifically, a therapeutically effective amount means an amount of crystals of the present invention or pharmaceutical compositions thereof effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any crystals of the present invention or pharmaceutical compositions thereof used in the methods of the invention, the therapeutically effective amount or dose can be estimated initially from cell culture assays. Then, the dosage can be formulated for use in animal models so as to achieve a circulating concentration range that includes the IC$_{50}$ as determined in cell culture (i.e., the concentration of the crystals of the present invention or pharmaceutical compositions thereof which achieves a half-maximal inhibition of the PK activity). Such information can then be used to more accurately determine useful doses in humans.

Toxicity and therapeutic efficacy of a crystal of the present invention or a pharmaceutical composition thereof can be determined by standard pharmaceutical procedures in cell cultures or experimental animals, e.g., by determining the IC$_{50}$ and the LD$_{50}$ (both of which are discussed elsewhere herein) for a subject crystal of the present invention or a pharmaceutical composition thereof. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active species that are sufficient to maintain the kinase modulating effects. These plasma levels are referred to as minimal effective concentrations (MECs). The MEC will vary for each crystal of the present invention or a pharmaceutical composition thereof but can be estimated from in vitro data, e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. A crystal of the present invention or a pharmaceutical composition thereof should be administered using a regimen that maintains plasma levels above the MEC for 10-90% of the time, preferably between 30-90% and most preferably between 50-90%.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

The compositions may, if desired, be presented in a pack or dispenser device, such as an FDA approved kit, which may contain one or more unit dosage forms containing the active ingredient. The pack may for example include metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions including a crystal of the present invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

It is also an aspect of this invention that a crystal of the present invention or a pharmaceutical composition thereof, might be combined with other chemotherapeutic agents for the treatment of the diseases and disorders discussed above. For instance, a crystal of the present invention or a pharmaceutical composition thereof, might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilin's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

A crystal of the present invention or a pharmaceutical composition thereof, can also be used in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

It is contemplated that a crystal of the present invention or a pharmaceutical composition thereof can also be used in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a crystal of the present invention or a pharmaceutical composition thereof could also be used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors such as anastrozole.

Finally, it is also contemplated that the combination of a crystal of the present invention or a pharmaceutical composition thereof will be effective in combination with mitoxantrone or paclitaxel for the treatment of solid tumor cancers or leukemias such as, without limitation, acute myelogenous (non-lymphocytic) leukemia.

The present invention is illustrated by the following examples. It is to be understood that the particular examples, materials, amounts, and procedures are to be interpreted broadly in accordance with the scope and spirit of the invention as set forth herein.

EXAMPLES

X-ray diffraction (XRD) patterns were measured on a Scintag X2 diffractometer (Thermo ARL, Ecublens, Switzerland) equipped with a theta-theta goniometer. Melting points were determined using a TA Instruments 2920 differential scanning calorimeter (TA Instruments, New Castle, Del.) with standard crimped pans and a heating rate of 10° C./minute. Hygroscopicity was assessed by dynamic moisture sorption gravimetry (DMSG) using a Controlled Atmosphere Microbalance (Pharmacia Corp., Kalamazoo, Mich.). All chemicals used are available from Aldrich Chemical Co., Milwaukee, Wis., unless otherwise specified. N-[2-(diethylamino)ethyl]-5-[(5-fluoro-1,2-dihydro-2-oxo-3H-indol-3-ylidene)methyl]-2,4-dimethyl-1H-pyrrole-3-carboxamide was prepared as the free base by a procedure similar to that described in Example 80 of PCT International Publication No. WO 01/60814 (Tang et al.).

Methods

Powder X-Ray Diffraction (XRD). Powder X-Ray diffraction was performed using a Scintag X2 Advanced Diffraction System operating under Scintag DMS/NT 1.30a and Microsoft Windows NT 4.0 software. The system uses a Copper X-Ray source maintained at 45 kV and 40 MA to provide $CuK(\alpha_1$ emission of 1.5406 Å and a solid-state Peltier cooled detector. The beam aperture was controlled using tube divergence and anti-scatter slits of 2 and 4 mm and detector anti-scatter and receiving slits of 0.5 and 0.2 mm width. Data was collected from 2 to 35° two-theta using a step scan of 0.03°/point with a one second per step counting time. Scintag round, top loading stainless steel sample cups with 12 mm diameter inserts were utilized for the experiments. Bulk drug was sampled as-is and placed into the sample tray without any preparation. Some specific samples were also handground in a mortar and pestle before they were run. Data analysis was completed using Origin 6.0 (Microcal Software, Northampton Mass.).

Dynamic Moisture Sorption Gravimetry (DMSG). DMSG isotherms were collected on the variable temperature controlled atmosphere microbalance. Approximately 10 mg samples were used in the balance. Samples were run as received. The humidity was sequentially set between 0 and 90% relative humidity (RH) in 3% RH steps. The mass was then measured every two minutes. The RH was changed to the next value when the mass of the sample was stable to within 0.5 microgram in 480 seconds. A Visual Basic program was used to control the data collection and export the information to an Excel spreadsheet.

Thermal Analysis. Differential Scanning Calorimetry (DSC) data was obtained by crimping the powdered sample into an aluminum DSC pan. Samples were run as received, sizes were about 1 mg. Temperatures were typically scanned to 320° C. at a scan rate of 10° C. per minute. The DSC was a TA Instruments 2920 calorimeter. The data analysis software used was TA's Universal Analysis V 1.1 OB.

Thermogravimetric Analysis (TGA) data was obtained on a TA instruments TGA 2950. Samples were equilibrated in the TGA at 25° C., with a 20° C. dew point for 30 minutes before the temperature program began. The temperature ramp was at 10° C./minute, but was scanned under TA's proprietary high-resolution conditions. This technique slows the scan rate when a transition is occurring, improving the ability of the instrument to resolve independent weight loss events.

Example 1

Preparation of the Anhydrous Crystal Form I of the L-Malic Acid Salt of N-[2-(Diethylamino)ethyl]-5-[(5-fluoro-1,2-dihydro-2-oxo-3H-indol-3-ylidene)methyl]-2,4-dimethyl-1H-pyrrole-3-carboxamide Preparation A: N-[2-(Diethylamino)ethyl]-5-[(5-fluoro-1,2-dihydro-2-oxo-3H-indol-3-ylidene)methyl]-2,4-dimethyl-1H-pyrrole-3-carboxamide (130 mg, 0.326 mMol) was added to 20 mL methanol, and the mixture was stirred. L-malic acid (47.2 mg, 0.352 mMol) was added, resulting in rapid dissolution of all the solids. The methanol was removed under reduced pressure to produce a poorly crystalline orange solid. Acetonitrile (5 mL) was added, and the slurry was stirred and heated for about 10 minutes. Stirring was continued while the slurry was allowed to cool to room temperature. The crystals were filtered and dried, resulting in 149 mg of solids (86% yield) of Crystal Form I.

Preparation B: N-[2-(Diethylamino)ethyl]-5-[(5-fluoro-1,2-dihydro-2-oxo-3H-indol-3-ylidene)methyl]-2,4-dimethyl-1H-pyrrole-3-carboxamide may be purified by an aqueous pH=11 wash prior to formation of the L-malic acid salt. A solution of the free base in a mixture of 80:20 n-butanol:water (v:v) was prepared at 80° C. After cooling to 20° C. and stirring for 1 hour, significant crystallization was observed. A sample was analyzed by PXRD and found to be Crystal Form I. Filtration, drying, and co-milling of the crystals resulted in 99% yield.

Example 2

Preparation of Crystal Form II of the L-Malic Acid Salt of N-[2-(Diethylamino)ethyl]-5-[(5-fluoro-1,2-dihydro-2-oxo-3H-indol-3-ylidene)methyl]-2,4-dimethyl-1H-pyrrole-3-carboxamide Crystals of Crystal Form I of the L-malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide (25 mg) were added to tetrahydrofuran (2 mL), followed by the addition of water (250 microliters). The mixture was heated to dissolve the crystals. The solvent was allowed to evaporate overnight, resulting in crystals of Crystal Form II.

Example 3

Preparation of the Anhydrous Crystal Form I of the L-Malic Acid Salt of N-[2-(Diethylamino)ethyl]-5-[(5-fluoro-1,2-dihydro-2-oxo-3H-indol-3-ylidene)methyl]-2,4-dimethyl-1H-pyrrole-3-carboxamide from Crystal Form II Acetonitrile (approximately 5 mL) was added to Crystal Form II (150 mg). The slurry was stirred and heated for about 10 minutes. Stirring was continued while the slurry was allowed to cool to room temperature. The crystals were filtered and dried, resulting in crystals of Crystal Form I.

Example 4

Solubility of Crystal Form I of the L-Malic Acid Salt of N-[2-(Diethylamino)ethyl]-5-[(5-fluoro-1,2-dihydro-2-oxo-3H-indol-3-ylidene)methyl]-2,4-dimethyl-1H-pyrrole-3-carboxamide The solubility of Crystal Form I of the L-malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide was determined to be 5 mg/mL in water at 25° C. This indicates that solubility should not be a limiting factor in bioavailability of the material.

The complete disclosure of all patents, patent applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of preparing an anhydrous crystal of a malic acid salt of N-[2-(diethylamino)ethyl]-5-[(5-fluoro-1,2-dihydro-2-oxo-3H-indol-3-ylidene)methyl]-2,4-dimethyl-1H-pyrrole-3-carboxamide of Crystal Form I having a characteristic X-ray diffraction data pattern in accordance with FIG. 1, the method comprising:

combining malic acid; N-[2-(diethylamino)ethyl]-5-[(5-fluoro-1,2-dihydro-2-oxo-3H-indol-3-ylidene)methyl]-2,4-dimethyl-1H-pyrrole-3-carboxamide; and a solvent; and inducing the salt to crystallize under crystallization conditions comprising one or more factors comprising: a difference between the initial and final temperatures of the crystallization solution of at most about 100° C.; a rate of cooling of at most about 50° C. per hour; no seeding; a supersaturation ratio of at most about 10; no precipitant; and/or combinations thereof.

2. The method of claim 1, wherein the malic acid is L-malic acid.

3. The method of claim 1, wherein the one or more factors comprise: a difference between the initial and final temperatures of the crystallization solution of at most about 50° C.; a rate of cooling of at most about 20° C. per hour; a supersaturation ratio of at most about 5; and/or combinations thereof.

4. The method of claim 3, wherein the one or more factors comprise: a difference between the initial and final temperatures of the crystallization solution of at most about 25° C.; a rate of cooling of at most about 2° C. per hour; a supersaturation ratio of at most about 1.5; and/or combinations thereof.

5. The method of claim 4, wherein the initial and final temperatures of the crystallization solution are the same.

6. The method of claim 1, wherein the solvent is selected from the group consisting of acetonitrile, methanol, ethanol, isopropanol, toluene, n-butanol, tetrahydrofuran, N,N-dimethylformamide, acetone, water, and combinations thereof.

* * * * *